United States Patent [19]

Garabedian

[11] Plant 5,178

[45] Jan. 17, 1984

[54] PLUM TREE GAR FANTASY

[76] Inventor: John M. Garabedian, 3104 Huntington Blvd., Fresno, Calif. 93747

[21] Appl. No.: 443,336

[22] Filed: Nov. 22, 1982

[51] Int. Cl.[3] ..... A01H 5/00
[52] U.S. Cl. ..... Plt./38
[58] Field of Search ..... Plt./38

*Primary Examiner*—James R. Feyrer
*Attorney, Agent, or Firm*—Huebner & Worrel

[57] ABSTRACT

A plum tree bearing very late ripening fruit which ripens about two weeks later than fruit of the Roysum variety (U.S. Plant Pat. No. 2,619) and which has yellowish-amber flesh diffused and mottled with red toward the skin and has a deep and extensive red to purplish-red skin coloration.

1 Drawing Figure

BACKGROUND OF THE VARIETY

The present invention relates to a new and distinct variety of plum tree which has been named "Gar Fantasy" for commercial marketing. The new variety is broadly characterized by bearing semi-freestone fruit having light yellowish-amber flesh diffused and mottled with red toward the skin and is more particularly characterized by its fruit being very late ripening, approximately two weeks later than fruit of the Roysum variety (U.S. Plant Pat. No. 2,619), and by the fruit of the new variety having a deep and attractive red to purplish-red skin coloration.

An important factor contributing to the success of a variety of plum tree bearing plums for the fresh market is that the fruit of the variety be attractive in appearance. Another important factor is that the variety bear such fruit at a time when other fruit with these desirable qualities is not available. Thus, the Roysum variety of plum tree has enjoyed substantially commercial success due to its fruit, which has various desirable qualities, ripening relatively late in the season for fresh plums. It is evident that a new variety bearing plums which have an attractive appearance and which ripen even later than those of the Roysum variety is especially desirable for commercial planting. Plums of the subject variety have flesh which, rather than being a uniformly light yellow color, as in the Roysum variety is mottled and diffused with red toward the skin and have an attractive exterior appearance with an extensive red to purplish-red coloration which is deeper in color than that of the Roysum variety.

ORIGIN AND ASEXUAL REPRODUCTION OF THE NEW VARIETY

The new variety of plum tree was discovered by me in 1968 as an open pollinated seedling of unknown parentage growing on a ranch owned by me located at Church and Greenwood Avenues, near the City of Sanger, in the County of Fresno, in the State of California. In 1971, I asexually reproduced the seedling by budding it onto seedling rootstock in 1971 on a ranch also owned by me at the intersection of Avenue 7 and Road 35 in the County of Madera, in the State of California and the tree and fruit characteristics resulting from such budding proved identical to those of the original seedling.

SUMMARY OF THE NEW VARIETY

The subject variety of plum tree (Prunus Salicina) bears very late ripening, semi-freestone fruit of medium to large size having flesh of light yellowish-amber color diffused and mottled with red toward the skin. The skin of plums of the subject variety have an attractive and extensive, 85 to 95 percent, red to purplish-red blush which is deeper in color than that of the Roysum variety. In relation to plums of the Roysum variety, plums of the subject variety are somewhat larger and have a shape which is longer and is cordate. The new variety is particularly distinguished by its fruits ripening approximately two weeks later than fruit of the Roysum variety.

BRIEF DESCRIPTION OF THE DRAWING

The accompanying drawing is a color photograph of mature plums of the subject variety together with a pair of representative twigs thereof showing characteristic leaves, one of the twigs having five of the plums, which bear a typical bloom attached thereto, two other plums being detached from the twigs with the bloom removed and being disposed to show the apex and the suture characteristics, and another detached plum being divided along the suture plane to show the flesh and stone characteristics.

DETAILED DESCRIPTION

Referring more specifically to the pomological details of the new and distinct variety of plum tree, the following have been observed under the ecological conditions prevailing in the above-designated ranch located at the intersection of Avenue 7 and Road 35 in the County of Madera and in the State of California. All of the color plate designations are by reference to the Maerz and Paul *Dictionary of Color,* Second Edition, 1950, common descriptive names also being used.

TREE

Size: Medium.
Vigor: Medium.
Form: Vase shaped, upright, spreading, open under usual pruning techniques.
Productivity: Productive.
Bearing: Regular.
Trunk: Medium in thickness and roughness.

Branches: Medium in thickness and roughness with shoots of current season smooth; color, gray 8-C-10 (Moose) with dull green striations 5-A-10 (Rose Beige 2, +); lenticels, medium in number, large in size, elongated transversely.

Shoot leaves: Large to medium in size; length, 10.52±0.78 cm; width, 5.07±0.56 cm; medium thickness; form, oval to broad oval, with apex acuminate and base more obtusely acuminate; nearly smooth; margin crenate; medium green in color, upperside 22-L-8, underside 20-E-5; petiole, thick to medium in thickness and long to medium, 1.47±0.18 cm, in length; glands, usually 2 in number (range 1 to 3); usually oppositely disposed on petiole near base of blade and/or on base of blade, medium in size, globose, green in color; stipules lacking when described.

Spur leaves: Medium in size; length 9.40±1.09 cm; width 3.36±0.61 cm; slightly obovate and occasionally oval in form with apex acuminate with base long acuminate, acute; margin crenate; medium thickness; nearly smooth; light green in color; petiole moderately thick and 1.35±0.30 cm in length; glands, usually 2 in number (range 1 to 3), disposed oppositely and usually at base of blade and, occasionally, apically on petiole, globose, medium to small in size and inconspicuous; green in color; stipules wanting.

Flower buds: Spurs very compact with numerous buds which are free, small, short, obovate and glabrous.

Flowers: Large in size and white in color; bloom late compared with other varieties, in 1982 first bloom was February 25 and last bloom was March 10.

FRUIT

Maturity: Approximately 2 weeks after Roysum variety (U.S. Plant Pat. No. 2,619), in 1982 picked September 23; described when hard on Sept. 24, 1982.

Size: Medium to large; uniform; diameter 5.79±0.34 cm axially, 5.94±0.22 cm in suture plane, 5.96±0.19 cm in cheek plane.

Form: Moderately variable; nearly symmetrical; nearly globose, varying from slightly oblatish to broadly cordate.

*Cheek aspect.*—Slightly oblatish to broadly oval to broad cordate with ventral edge usually somewhat longer.

*Suture aspect.*—Broad ovate to, usually, broad cordate to cordate.

*Axial aspect.*—Broad elliptic, nearly round.

*Suture.*—Inconspicuous shallow groove from base to apex with slight depression beyond pistil point.

*Ventral surface.*—Slightly rounded; lipped toward base; lips usually slightly unequal.

*Cavity.*—Flaring, elongated in suture plane with suture showing on top on one side, no markings, depth 1.09±0.12 cm, breadth 2.62±0.11 cm.

*Base.*—Broad, truncate.

*Apex.*—Usually moderately prolonged to rounded; pistil point, apical.

Skin: Medium in thickness and toughness; tenacious to flesh; no tendency to crack in dry season; pubescence wanting; medium bloom; ground color 9-I-3 with 85 to 95 percent blush of 5-A-7 (Barberry) to 56-L-12; dots numerous apically, inconspicuous, small, aeolar.

Flesh:

*Color.*—Light yellowish-amber with reddish tinge, ground color 9-I-3 diffused and mottled next to skin with red 5-L-8; surface of pit cavity amber.

*Amygdalin.*—Wanting.

*Juice.*—Scant.

*Texture.*—Medium in hardness, fine, melting.

*Fibers.*—Few and fine.

*Ripening.*—Even.

*Flavor.*—Mild.

*Aroma.*—Wanting.

*Eating quality.*—Good.

Stone: Semi-free, adheres to flesh along ventral edge and upper half of sides; no tendency to split in dry season.

*Fibers.*—Short.

*Size.*—Medium, length 2.19±0.09 cm, breadth 1.60±0.07 cm, thickness 0.92±0.03 cm.

*Form.*—Oval with cheek aspect oval but flattened to slightly recurved basally, with suture aspect narrowly ovate to oval, and with axial aspect oval; base straight; hilum narrow and oval; apex bluntly acute to short acuminate.

*Surface.*—Lightly roughened; irregularly furrowed, ridged near base, ridges low and variable toward base.

*Ventral edge.*—Thin.

*Dorsal edge.*—Narrow with deep groove to above center.

*Ventral suture.*—Narrow; suture line a shallow groove shallower apically, variable and often much eroded; rounded to elevated wings with a shallow groove subtending laterally.

*Dorsal suture.*—Groove relatively wide and deep from base, or nearly so, nearly to apex with the sides of the groove slightly eroded.

*Color.*—Light brown, slightly variable from 10-G-7 to 11-D-10.

Use: Market, dessert and cullinary.

Keeping quality: Good.

Shipping quality: Good.

Resistance to insects and disease: Not observed.

Although the new variety of plum tree possesses the described characteristics as a result of the growing conditions prevailing in Madera County, Calif. in the San Joaquin Valley, it is to be understood that variations of the usual magnitude in characteristics incident to growing conditions, fertilization, pruning and pest control are to be expected.

Having thus described and illustrated my new variety of plum tree, I claim:

1. A new and distinct variety of plum tree generally characterized by bearing very late ripening, semi-freestone fruit of medium to large size and cordate shape, the flesh of such fruit being yellowish-amber in color and diffused and mottled with red toward the skin, the new variety being particularly characterized as to novelty by bearing fruit ripening approximately two weeks later than fruit of the Roysum variety (U.S. Plant Pat. No. 2,619) and having skin with an extensive and attractive blush of a deeper red to purplish-red than that of the Roysum variety.

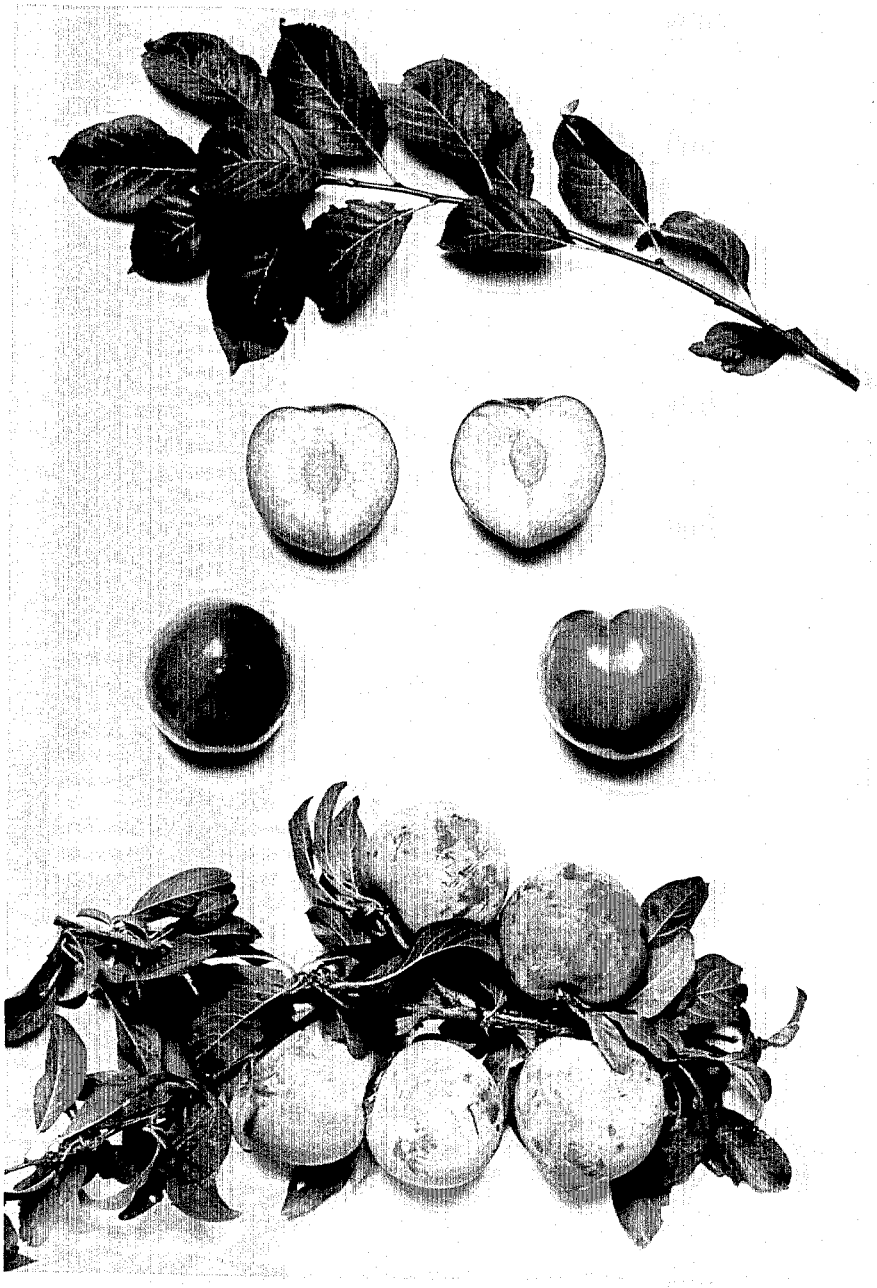

* * * * *